United States Patent [19]

MacLeay

[11] Patent Number: 4,585,857

[45] Date of Patent: Apr. 29, 1986

[54] BLEACH OXIDATION OF N,N′-DI-T-OCTYLSULFAMIDE TO DI-T-OCTYLDIAZENE

[75] Inventor: Ronald E. MacLeay, Williamsville, N.Y.

[73] Assignee: Pennwalt Corporation, Philadelphia, Pa.

[21] Appl. No.: 681,732

[22] Filed: Dec. 14, 1984

[51] Int. Cl.$^4$ ............................................. C07C 107/02
[52] U.S. Cl. ................................... 534/587; 534/573; 534/838; 564/118
[58] Field of Search .................... 534/573, 587, 838

[56] References Cited

PUBLICATIONS

Hitzler et al., Chemical Abstracts, vol. 92, 199050u, (1980).
Toyama et al., Chemical Abstracts, vol. 88, 120602m, (1978).

Primary Examiner—Floyd D. Higel

[57] ABSTRACT

Di-t-octyldiazene is prepared in improved yield, purity and economics by oxidizing N,N′-di-t-octylsulfamide with sodium hypochlorite solution in a strongly basic medium at a temperature of 65°–90° C. in a minimal amount of hydrocarbon or chlorinated hydrocarbon solvent for about 2 to 5 hours until completion of the reaction. The employment of phase transfer catalysts or t-butyl alcohol in the oxidation is optional. Di-t-octyldiazene is used as a polymerization initiator for vinyl monomers and as a curing agent for unsaturated polyester resins.

5 Claims, No Drawings

BLEACH OXIDATION OF N,N'-DI-T-OCTYLSULFAMIDE TO DI-T-OCTYLDIAZENE

BACKGROUND OF THE DISCLOSURE

1. Field of the Invention

This invention relates to an improved process of preparing di-t-octyldiazene by oxidizing N,N'di-t-octylsulfamide with sodium hypochlorite and caustic and optionally in the presence of a phase transfer catalyst and/or t-butyl alcohol at a temperature of 65°–90° C. in a minimal amount of solvent.

2. Prior Art

Among the many t-azoalkanes (I) known,

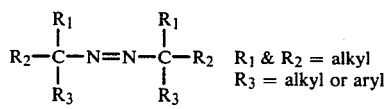

$$R_1 \text{ \& } R_2 = \text{alkyl}$$
$$R_3 = \text{alkyl or aryl}$$

di-t-octyldiazene (II) is a particularly attractive compound to make commercially.

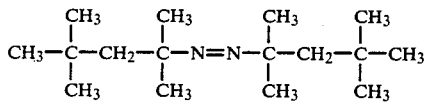

Di-t-octyldiazene is a known compound whose rate of thermolysis was studied by Timberlake and co-workers (B. K. Bandlish, A. W. Garner, M. L. Hodges and J. W. Timberlake, J. Am. Chem. Soc. 97, p.5856–5862, 1975). From their thermolysis data the 10 hr. half-life temperature ($t_{\frac{1}{2}}$) was calculated to be about 107.5° C. Thus, its decomposition temperature falls into a very useful temperature range for initiating vinyl polymerizations. The compound is a liquid at room temperature and is relatively non-volatile. Since it does not contain any cyano groups as do the commercial symmetrical and unsymmetrical azonitriles, it should not generate any toxic residues upon decomposition. Despite the attractiveness of this compound, no evidence was found that di-t-octyldiazene (II) is being produced or used commercially despite the commercial availability of t-octylamine. This is because prior to the present invention there wasn't any commercially feasible route to prepare di-t-octyldiazene.

In 1965 R. Ohme and E. Schmitz developed a general synthetic method for the preparation of azoalkanes (R. Ohme and E. Schmitz, Angew Chem Int. Ed. Engl. 4, p.433, 1965). They found that the dialkylamides of sulfuric acid in a solution of N alkali react with 2 moles of NaOCl at 20°–60° C., to form aliphatic azo compounds. They prepared the low molecular weight azopropane, azobutane, and azocyclohexane in this manner.

In 1967 R. Ohme and H. Preuschof studied the mechanism of this oxidation as well as the oxidation of N,N'-disubstituted sulfamides and monosubstituted sulfamides (R. Ohme and H. Preuschkof, Liebigs Ann. Chem. 713, p.74–86, 1968). During the course of their investigation they prepared 2,2'-azoisobutane in 84% yield by oxidizing N,N'-di-tert-butylsulfamide in 2N NaOH with 2 equivalents of NaOCl at 60° C. J. C. Stowell prepared 2,2'-azoisobutane in 84% yield by running a similar type reaction for 3 hours in pentane (J. C. Stowell, J. Org. Chem. 32, p.2360, 1967).

In 1972 J. W. Timberlake and co-workers attempted to prepare di-t-octyldiazene and di-t-heptyldiazene by this route but were unsuccessful (J. W. Timberlake, M. L. Hodges and K. Betterton, Synthesis 1972, p.632–34). Treatment of either N,N'-bis[2,4,4-trimethyl-2-pentyl]sulfamide (i.e. N,N'-di-t-octylsulfamide) or N,N'-bis[2,3,3-trimethyl-2-butyl]sulfamide (i.e. N,N'-di-t-heptylsulfamide) under the conditions specified in Ohme's articles gave no azo compound. Timberlake recognized that the oxidation of sulfamides to azo compounds was not adaptable to all azos. The conditions were too vigorous for isolating unstable azo compounds and solubility problems in several cases led to quantitative return of starting sulfamides. Therefore Timberlake developed a more complex method of converting the N,N'-dialkylsulfamides into azoalkanes. He used a completely homogeneous mixture with potassium t-butoxide as the base, t-butyl hypochlorite as the chlorinating agent, and t-butanol as the solvent. He also developed a heterogeneous mixture with sodium hydride as the base and t-butyl hypochlorite as the chlorinating agent in an ether/pentane solvent. Timberlake prepared di-t-octyldiazene in 78% yield by treating the sulfamide with a slurry of 2 eqs. of sodium hydride in pentane for 2 hours at room temperature, the reaction cooled to 0° C. and 2 eqs. of t-butyl hypochlorite added dropwise and the mixture stirred overnight. The excess sodium hydride was then destroyed by the careful addition of water and the pentane solution of the azo chromatographed over alumina. The azo was then distilled to obtain a 78% yield. Although the process was very useful for preparing laboratory scale samples, it was hardly practical for development on a commercial scale.

In 1974 C. Ruchardt and co-workers proclaimed that they had a new simple, high yield procedure for the large scale synthesis of tert-azoalkanes (I) from readily available chloroazoalkanes and trialkyl- or triphenylaluminum (W. Duismann, H. Beckhaus and C. Rüchardt, Liebigs Ann. Chem. 1974, p.1348–1356). Rüchardt stated that the t-azoalkanes are excellent generators of free radicals but representatives of this class of compounds have still not acquired any significance as initiators in industry solely due to the difficulty in preparing them. The known syntheses are tedious and frequently produce low yields. None of the known preparative procedures are suited to general large-scale synthesis of t-azoalkanes. Rüchardt felt his process would overcome these shortcomings. Rüchardt and co-workers produced 28 different symmetrical t-azoalkanes by this process. They prepared di-t-octyldiazene in 82% yield.

In 1976 M. Prochazka prepared di-t-octyldiazene by the oxidation of t-octylamine with $IF_5$ (M. Prochazka, Collect. Czech. Chem. Commun. 1976, 41(5), p.1557–1564 (Eng); C.A. 86, p.338c, 1977). The compound was prepared on a small scale for comparison of its rate of decomposition with other t-azoalkanes Prochazka prepared.

In 1978 a Japanese patent described a process for oxidizing N,N'-di-t-octylsulfamide with bleach and caustic in the presence of a phase transfer catalyst (Japan Kokai 77, 128, 305; C.A. 88, p.120602m, 1978). The reaction was run at 40° C. and required 10 hours to complete. This was the first indication that di-t-ocyldiazene could be prepared by the aqueous bleach route. The process required a phase transfer catalyst and a long reaction period.

In early 1982 a European patent (European Pat. No. 0,006,972) was published describing a photopolymerization process. In the patent, there is a description of the preparation of 2,2'-azobis(2,4,4-trimethylpentane) which is also referred to as di-t-octyldiazene. The di-t-octyldiazene was prepared by oxidizing N,N'-di-t-octylsulfamide with bleach and caustic solution for 20 hours at 35° C. The yield was only 50% after purification by vacuum distillation. A complete description of the experiment was not provided. However, in other examples in the patent, 2,2'-azobis-2-methylbutane and 1,1'-di-methyl-azocyclopentane were prepared by oxidizing the corresponding sulfamides with sodium hypochlorite solution in the presence of 10 parts pentane to 1 part t-butyl alcohol. The reactions were stirred for 24 hours at 35°–40° C. Specific % yields were not reported.

In 1971 A. Ohno and co-workers reported the preparation of azobis-(2-propyl)-2-propane by sodium hypochlorite oxidation of the corresponding sulfamide (A. Ohno, N. Kito and Y. Ohnishi, Bull. Chem. Soc. Japan, 1971, 44, p.470–474). The azo was obtained in 38% yield after stirring 7.0 grams of the sulfamide in 50 ml of hexane with 150 ml of 10% NaOCl for 35 hours at room temperature. The crude product was purified by distillation.

Although these reactions used cheap raw materials, i.e. sodium hydroxide and sodium hypochlorite instead of sodium hydride and t-butyl hypochlorite, the reaction time required to complete the reaction was much too long to be commercially attractive. Therefore, despite the fact that di-t-octyldiazene has been made by five various routes, there is no commercially attractive route to di-t-octyldiazene. In addition, there is no indication that the oxidation of the sulfamide can be carried out in high yield and short reaction time using the sodium hypochlorite-sodium hydroxide system. In fact the prior art indicates it cannot be done.

SUMMARY OF THE INVENTION

This invention is directed to an improved process of preparing di-t-octyldiazene comprising oxidizing N,N'-di-t-octylsulfamide with sodium hypochlorite (bleach) in a strongly basic solution at a temperature of 65°–90° C. in the absence of or in the presence of a minimum amount of a hydrocarbon or chlorinated hydrocarbon solvent (i.e., less than 4 parts solvent per part sulfamide) for about 2 to 5 hours until completion of the reaction. The crude product is given an aqueous sodium bisulfite wash to remove chloramine impurities. The improvements in the process will make it economically feasible to produce di-t-octyldiazene on a commercial scale.

DETAILED DESCRIPTION OF THE INVENTION

Since the N,N'-di-t-octylsulfamide is conveniently prepared and isolated in a hydrocarbon solvent such as pentane, hexane, cyclohexane, or heptane, the solvent content can be reduced to the desired range by evaporation under reduced pressure or by distillation, either before the oxidation reaction is started or during the course of the reaction. The rate of oxidation can be conveniently adjusted so that proper reaction control can be maintained by simply adjusting the reaction temperature and the rate of solvent removal. From maximum rate of oxidation, it is desirable to reduce the solvent to sulfamide ratio to a range of 2:1 to 0.5:1. The reaction will occur more rapidly if the solvent is completely removed but this is neither necessary nor advantageous. Operating above the 4:1 ratio of solvent to sulfamide slows the reaction down considerably and leads to lower assay product.

Although only two equivalents of bleach and one equivalent of caustic per equivalent of sulfamide are necessary, it is advantageous to use excess bleach and caustic to speed up the reaction and insure complete oxidation since these raw materials are relatively inexpensive. Generally a mole ratio of 2.5–2.8:1 of bleach to N,N'-di-t-octylsulfamide and a mole ratio of 2.0–2.5:1 of caustic to sulfamide work well without being unduly wasteful. The excess bleach insures completion of reaction in a reasonable amount of time and the excess caustic stabilizes the bleach at the higher reaction temperatures. Since the ten hour $t_{\frac{1}{2}}$ of di-t-octyldiazene is about 107.5° C., it is advisable to hold the reaction temperature at 90° C. or below to prevent thermal decomposition of the azo that forms. Normally, temperatures of 65°–75° C. are adequate for oxidizing the N,N'-di-t-octylsulfamide in a short period of time, that is, in less than 5 hours with 2 to 4 hours being preferred.

The starting N,N'di-t-octylsulfamide is prepared from commercially available t-octylamine and sulfuryl chloride using either the method of Stowell (J. C. Stowell, J. Org. Chem. 32, p.2360, 1967) or of Timberlake (J. W. Timberlake, J. Alender, A. W. Garner, M. L. Hodges, C. Ozmeral and S. Syilagyi, J. Org. Chem. 46, p.2082–2089, 1981). The reaction is preferably run in hexane and the product isolated as a hexane solution. The hexane solution of the sulfamide can be concentrated prior to oxidizing the sulfamide or it can be concentrated during the oxidation.

The sulfamide reaction can be run in hydrocarbon or chlorinated hydrocarbon solvents. Pentane, hexane, heptane, cyclohexane, and methylene chloride are preferred for the reaction. Hexane is the most preferred solvent for the reaction because it boils at a desirable temperature for the oxidation step and residual hexane can be readily removed from the product by stripping under reduced pressure.

It is desirable to use 14–15% sodium hypochlorite in the oxidation. Normally, higher concentrations of bleach are not commercially available. Weaker solutions of bleach also work, but smaller batch sizes have to be run in a common reactor to accommodate the larger volume of weak bleach required. Sodium or potassium hydroxide are suitable bases for maintaining the high pH required throughout the course of the reaction but sodium hydoxide is preferred on an economical basis.

The use of phase transfer catalysts and t-butyl alcohol are optional. The presence of a small amount of a phase transfer catalyst eliminates foaming during the oxidation step. An antifoaming agent would accomplish the same end.

Normally small amounts of N-chloramines form in the oxidation step. Therefore, it is advisable to wash the crude azo with sodium bisulfite solution to reduce these bothersome impurities back to t-octylamine which goes out in the acidic bisulfite solution.

This improved oxidation process works for other difficult to oxidize N,N'-di-t-alkylsulfamides such as N,N'-di-t-amylsulfamide. Examples IX and X demonstrate the reduction in reaction time required to oxidize N,N'-di-t-amylsulfamide as the reaction temperature is increased and the solvent distilled off.

Di-t-octyldiazene is a useful free radical generator which has been used to cure a polyester resin to a hard Barcol at 250° F. The process described in this invention is applicable to other difficult to oxidize N,N'-di-t-alkylsulfamides such as N,N'-di-t-heptylsulfamide, N,N'-di-t-amylsulfamide, N,N'-di-(1-methylcyclopentyl)sulfamide, and N,N'-di-t-hexylsulfamide (J. W. Timberlake, M. L. Hodges and K. Betterton, Synthesis 1972, p.632–34; European Pat. No. 0,006,972; A. Ohno, N. Kito and Y. Ohnishi, Bull. Chem. Soc. Japan, 1971, 44, p.470–474).

EXAMPLES

The following examples will demonstrate the effect of reaction temperature and solvent concentrations on the rate of oxidation of N,N'-di-t-octylsulfamide with sodium hypochlorite and caustic. The conversion of sulfamide to di-t-octyldiazene was followed by gas chromatography. The solvent peaks were not integrated in the scans. The % conversion was estimated by using the area % integration of the azo peak. The sulfamide formed some intermediate peaks which converted to azo upon further reaction. There were also small amounts of impurities generated during the course of the reactions. These were removed in most cases with an aqueous sodium bisulfite wash. Therefore, the difference between the % azo in the scan and 100% was not necessarily the % sulfamide unreacted. Nevertheless, the disappearance of the sulfamide peak and the intermediate peaks was easily monitored on a 18 inch×⅛ inch 3% OV-17 column. Normally the temperature was programmed from 80° C. to 200° C. at 8° or ±16° C./min. The compounds were very easy to separate under a variety of gas chromatograph conditions. A Hewlett Packard 5710A gas chromatograph coupled to a 3380S integrator was used for the monitoring.

Final assays were determined accurately by gas chromatography using analytically pure standards and internal standards. It should be noted that the area % assays in the Examples are not correct assays (see Examples II, III, IV); they are used to monitor the course of reaction.

EXAMPLE I

This example demonstrates the increased oxidation rate obtained at 65° C. It also indicates the inability to obtain high assay material when the hexane solvent is not removed during the oxidation.

N,N'-di-t-octylsulfamide (10.1 grams, 0.0315 m) was dissolved in 30 ml of warm hexane in 250 ml 3 neck flask equipped with a magnetic stirrer, thermometer, and reflux condenser. A solution of 5.0 grams (0.063 m) of 50% aqueous NaOH in 70 grams (0.9 m) of 10% aqueous NaClO was added followed by 0.5 grams of Adogen 464 phase transfer catalyst. The reaction was stirred vigorously and warmed to 40° over 15 minutes and stirred 1 hour at 40°–48° C. VPC analysis indicated no azo had formed. The reaction was then warmed to 65° C. over ½ hour. Only 1.5% of azo was formed. After ½ hour at 65° C. there was 11% of azo formed. After 1¼ hours at 65° C. there was 40% azo, after 2¼ hours 63%, after 3½ hours 91%, and after 5½ hours 93% azo by area %. The hexane solution was separated and the crude azo worked up and isolated. The crude product weighed 7.6 grams and assayed 93% by area %. However, upon accurate analysis using an internal standard, it only assayed 72.9%. Obviously, it contained some high boilers that didn't show up on the VPC scan.

The reaction was repeated with almost identical results. The reaction was complete after 4 hours but the corrected assay was only 80%.

For the sake of comparison the following experiment was run to demonstrate the ineffective oxidation of N,N'-di-t-octylsulfamide in hexane at temperatures below 60° C. in the presence of a phase transfer catalyst.

N,N'-di-t-octylsulfamide (28.3 grams, 0.088 m) was dissolved in 50 ml of hexane in a 500 ml round bottom flask equipped with a magnetic stirrer, thermometer and reflux condenser. A solution of 16 grams (0.2 m) of 50% NaOH in 150 grams (0.2 m) of 10% NaClO was added followed by 0.5 grams of Adogen 464 phase transfer catalyst. The reaction was stirred vigorously for 15 minutes without any apparent reaction. The reaction was warmed to 45° C. on a warm water bath over 15 minutes and then stirred 2 hours at 40°–45° C. A gas chromotographic scan after the first hour indicated that there was about 6% of azo present. The reaction was stirred overnight without any external heating. After stirring overnight, the % azo increased to 8%. The reaction was warmed back up to 50° C. for an additional 8¼ hours. After 4 hours at 45°–50° C. the azo peak increased to 30% and by the end of the day it had increased to 64%. The reaction was allowed to stir overnight for a second night at room temperature. By the next morning the azo peak had increased to 71%. The reaction mixture was transferred to a separatory funnel and the bleach layer separated. The hexane solution was washed with water and saturated NaHCO₃ solution, dried over anhydrous Na₂SO₄, filtered, and heated on a rotating evaporator under reduced pressure to strip off the hexane. The residue was a yellow-green liquid which weighed 24.1 grams but only assayed 70% by area %.

EXAMPLE II

This example demonstrates that the phase transfer catalyst in Example I was not necessary to obtain a fast reaction rate.

The reaction of Example I was repeated except that the Adogen 464 was not used. VPC analysis indicated the reaction was complete after reacting 3½ hours at 65° C. The crude product was worked up and isolated in the same manner as before. The crude product assayed 93.2% by area % but only 78.3% by internal standard. The results were very similar to those obtained in Example I with a phase transfer catalyst.

EXAMPLE III

This example demonstrates how the N,N'-di-t-octylsulfamide is prepared in hexane and then oxidized without isolating the sulfamide. The reaction was run without a phase transfer catalyst.

Into a 1000 ml 3-neck round bottom flask were added 84.0 grams (0.62 m) of 95% t-octylamine and 200 ml of hexane. The flask was equipped with a mechanical stirrer, thermometer, and 25 ml pressure equalizing dropping funnel and was placed in a dry ice-isopropanol bath. The solution was cooled to −20° C. and then 20.9 grams (0.15 m) of 97% sulfuryl chloride, diluted to 25 ml with hexane, was added dropwise over 20 minutes from a dropping funnel while holding the reaction temperature below 0° C. After the addition was completed, the isopropanol bath was removed and the reaction allowed to warm to 10° C. over 10 minutes. A warm water bath was used to raise the temperature to 45° C. The material caked in the necks of the flask was rinsed down with about 50 ml of hexane and the reaction was stirred 20 minutes at 40°–50° C. Then 100 ml of warm water was added. All the solids dissolved. The reaction mixture was transferred to a separatory funnel and the aqueous layer was separated and saved for t-octylamine recovery. The hexane solution was washed with 50 ml 10% HCl to remove any excess t-octylamine and the acid layer added to the aqueous layer.

The hexane solution of the N,N'-di-t-octylsulfamide was transferred to a 1 liter 3-neck round bottom flask and a solution of 30 grams (0.38 m) of 50% NaOH in 300 grams of 10% NaClO was added. The flask was equipped with a magnetic stirrer, thermometer, and reflux condenser. The flask was lowered into a preheated 80° C. oil bath and the contents were stirred vigorously. The reaction was monitored by gas chormatography. It took approximately ½ hour for the contents to reach a gentle reflux. During the course of the reaction, the temperature rose to 68° C. and there was considerable foaming in the flask. The bath had to be lowered and the reaction mass was cooled below 65° C. so that the foaming would subside. The reaction started out very slowly and required 5½ hours of gentle refluxing before the oxidation was completed. The reaction mass was cooled to 30° C. and transferred to a separatory funnel. The bleach layer was separated. The hexane solution was washed twice with water, and once with a 15% NaHSO₃ solution, water, and saturated NaHCO₃ solution. The hexane solution was dried over anhyrous sodium sulfate, filtered, and heated on a rotating evaporator under reduced pressure to strip off the hexane. The residue weighed 33.9 grams and assayed 88.5% by area %. It assayed 77.6% by internal standard. The correct yield was 26.3 grams (69% overall yield).

EXAMPLE IV

This example is a repeat of Example III except that a phase transfer catalyst was used in the oxidation to eliminate the foaming; after 3¼ hours, the reflux condenser was replaced with a distilling head and most of the hexane was distilled off from the reaction mixture.

The N,N'-di-t-octylsulfamide was prepared in the same manner as in Example IV except that only 150 ml of hexane were used in the reaction and the reaction temperature was held below 15° C. instead of 0° C.

The hexane solution of the sulfamide was oxidized with a solution of 30 grams of 50% NaOH in 300 grams of 11% NaClO using 0.2 grams of Adogen 464. The reaction was refluxed for 3¼ hours in the same nammer as in Example III. There was no foaming present. At this point the gas chromatograph indicated only 22% conversion to azo. Therefore, the reflux condenser was replaced by a distilling head connected to a downward condenser and the hexane was allowed to distill off. After 2 hours of additional stirring, the bleaching power of the aqueous layer was rather weak so an additional 80 grams of 9% NaClO were added and the reaction mass was stirred an additional hour. The reaction was cooled to 30° C. and worked up as in Example III. After stripping, the residue weighed 30.7 grams and assayed 92.2% by the internal standard method. The corrected yield was 28.3 grams (74.2% yield).

EXAMPLE V

This example is essentially a repeat of Example IV except that the distilling head was put on the flask at the beginning of the oxidation and the hexane began to distill off as soon as the reaction got warm enough.

The N,N'-di-octylsulfamide was prepared in the same manner as in Example IV except 200 ml of hexane and 89.9 grams (10% excess) of 95% t-octylamine were used.

The hexane solution of the sulfamide was oxidized with a solution of 30 grams of 50% NaOH in 300 grams of 13.9% bleach using 0.5 grams of Adogen 464 and 5 grams of t-butyl alcohol. The reaction flask was lowered into an 80° C. oil bath and the reaction mass was stirred vigorously for 2 hours while distilling off the hexane. It took about ½ hour before most of it had distilled off. Very little reaction occurred in the first ½ hour. The oxidation was about 85% complete at the end of 1 hour and essentially complete (by VPC analysis) at the end of 1½ hours. The reaction was stirred an additional ½ hour to insure complete oxidation but there was no change in the VPC scan. The reaction was cooled to 30° C. and worked up as in Example III. After high vacuum stripping, the residue weighed 32.4 grams and assayed 96.8% by internal standard. The correct yield was 31.4 grams (82.4% yield).

The reaction was repeated two more times using only 5% excess t-octylamine. The crude product assayed 95.6% and 95.9% and the corrected yields were 81.8% and 83% respectively.

EXAMPLE VI

This Example is essentially a repeat of Example V. The reaction was monitored by gas chromatography and the extent of reaction compared versus the amount of hexane distilled off. A phase transfer catalyst was not used in the oxidation step.

The N,N'-di-t-octylsulfamide was prepared in the same manner as in Example V except 200 ml of hexane were used.

The hexane solution of the sulfamide was oxidized with a solution of 30 grams of 50% NaOH in 225 grams of 13.9% bleach using 5 grams of t-butyl alcohol. The reaction flask was lowered into an 80° C. oil bath and the reaction mass was stirred vigorously. As the reaction mass heated up, the hexane began to distill off and was collected in a graduate and was measured at 15 minute intervals. At the same time, the reaction mass was sampled and injected into the gas chromatograph. A 0.25 minute delay was applied to the integrator so that the solvent peak would not integrate. The % azo formed was qualitatively determined by integrating the rest of the scan. The results are summarized in Table I. As the reaction progressed (about 50 minutes), the reaction mixture began to foam excessively; temperature of the oil bath had to be lowered and the stirring was stopped periodically to prevent the reaction mixture from foaming out of the flask. After 90 minutes, the reaction was essentially completed and the foaming had died out. The reaction mass was stirred an additional 45 minutes to insure completion of reaction. The reaction was cooled to 30° C. and worked up as in Example III. After high vacuum stripping, the residue weighed 31.9 grams and assayed 94.3% by internal standard. The corrected yield was 30.1 grams (79.0%).

TABLE I

| Reaction Time (minutes) | Bath Temp. °C. | Reaction Temp. °C. | % Azo Formed (Area %) | ml Hexane Collected |
|---|---|---|---|---|
| 0 | 78 | 25 | — | — |
| 30 | 77 | 61 | 0 | 25 |
| 45 | 79 | 64 | 28.1 | 105 |
| 60 | 77 | 73 | 64.4 | 155 |
| 75 | 74 | 75 | 92.2 | 170 |
| 90 | 71 | 67 | 97.2 | 175 |

TABLE I-continued

| Reaction Time (minutes) | Bath Temp. °C. | Reaction Temp. °C. | % Azo Formed (Area %) | ml Hexane Collected |
|---|---|---|---|---|
| 105 | 76 | 65 | 98.5 | 175 |
| 120 | 78 | 68 | 99.0 | 175 |
| 135* | 78 | 68 | 99.5 | 175 |

*Removing the delay on the integrator and reinjecting a sample of the organic layer at the end of the reaction indicated it still contained about 39% hexane despite the fact distillation had ceased.

EXAMPLE VII

This Example is a repeat of Example VI except that there wasn't any t-butyl alcohol present in the oxidation. The reaction was monitored by gas chromatography and the extent of reaction was compared with the amount of hexane distilled in Table II. Foaming problems were encountered during the oxidation due to the lack of a phase transfer catalyst. After high vacuum stripping, the residue weighed 31.9 grams and assayed 94.3% by internal standard. The corrected yield was 30.1 grams (79.0%).

TABLE II

| Reaction Time (minutes) | Bath Temp. °C. | Reaction Temp. °C. | % Azo Formed (Area %) | ml Hexane Collected |
|---|---|---|---|---|
| 0 | 70 | 25 | — | — |
| 30 | 78 | 62 | 0 | 10 |
| 45 | 78 | 63 | 0.8 | 35 |
| 60 | 78 | 63 | 3.9 | 65 |
| 90 | 78 | 73 | 48.1 | 160 |
| 105 | 80 | 85 | 94.8 | 188 |
| 120 | 82 | 76 | 98.0 | 190 |
| 135 | 81 | 71 | 98.1 | 190 |
| 150 | 80 | 69 | 98.1 | 190 |

EXAMPLE VIII

Curing an Unsaturated Polyester-Styrene Resin With Di-t-Octyldiazene

An unsaturated polyester resin was prepared by reacting maleic anhydride (1.0 mole), phthalic anhydride (1.0 mole), and propylene glycol (2.2 moles) until an acid number of 45-50 was obtained. To this was added hydroquinone at a 0.013% concentration. Seven parts of this unsaturated polyester was diluted with 3 parts of monomeric styrene to obtain a homogeneous blend having a viscosity of 13.08 poise and a specific gravity of 1.14.

To 20 grams of this blend was added 0.28 gram of crude di-t-octyldiazene; the mixture was stirred well with a wooden spatula. The sample was poured into a test tube and placed in a 121° C. oil bath. The internal temperature was recorded as a function of time and a peak exotherm of 229° C. was reached in 5.0 minutes indicating that an excellent cure of the unsaturated polyester-styrene resin blend had occurred.

Without an initiator, no cure of the resin blend had occurred even after 30 minutes.

EXAMPLE IX

This Example demonstrates the oxidation of N,N'-di-t-amylsulfamide at 65° C. in the presence of a phase transfer catalyst.

N,N'-di-t-amylsulfamide (9.5 grams, 0.04 m) was slurried in 40 ml of hexane in a 3 neck 500 ml round bottom flask equipped with a magnetic stirrer, thermometer, and reflux condenser. A solution of 10 grams of 50% NaOH in 150 grams of 13.9% bleach was added. The flask was lowered into a preheated oil bath (73° C.) and was stirred vigorously. The extent of reaction was followed by gas chromatography. The gas chromatographic scans were a qualitative indication of how long the reaction had to be refluxed to complete the oxidation. The scans indicated that the reaction was completed after refluxing for 5 hours at 64°-65° C. The reaction was refluxed an additional ½ hour to insure complete reaction. The reaction mixture was cooled to room temperature and was transferred to a separatory funnel. The bleach layer was separated from the hexane solution layer; the hexane layer was washed with 50 ml portions of water, 15% $NaHSO_3$ solution, and saturated $NaHCO_3$ solution and was dried over anhydrous $Na_2SO_4$. The hexane solution layer was filtered and the hexane was stripped off on a rotating evaporator under reduced pressure at 10° C. The crude product weighed 5.1 grams and assayed 93.3% by area % on the gas chromatograph. The crude % yield was 69.6%. The reaction required 5 hours to run.

This is a comparative experiment which demonstrates the ineffective oxidation of N,N'-di-t-amylsulfamide in pentane at 30°-40° C. in the presence of a phase transfer catalyst and t-butanol. The N,N'-di-t-amylsulfamide was prepared from t-amylamine and sulfuryl chloride in hexane.

N,N'-di-t-amylsulfamide (9.4 grams, 0.04 m) was slurried in 40 ml of pentane in a 3 neck 500 ml round bottom flask equipped with a magnetic stirrer, thermometer, and reflux condenser. A solution of 10 grams of 50% NaOH in 150 grams of 13.9% NaClO was added followed by 4 grams of t-butanol. The reaction was stirred for 2¼ hours at 25° C. A gas chromatographic scan indicated essentially no reaction had occurred. Then 0.5 gram of Adogen 464 phase transfer catalyst was added and the reaction mass was stirred 2½ hours at 30° C. By this point all the sulfamide had dissolved and a gas chromatographic scan indicated that about 30% conversion to di-t-amyldiazene had occurred. The reaction was warmed to 36° C. and refluxed gently for an additional 3¼ hours. Gas chromatographic analysis indicated about 65% conversion to di-t-amyldiazene. The reaction was stirred overnight at room temperature and the conversion increased to about 85%. The reaction was warmed to 40° C. and stirred until gas chromatographic analysis indicated that the oxidation was completed. This required an additional six hours. The reaction mixture was cooled to room temperature and transferred to a separating funnel. The bleach layer was separated from the pentane solution layer; the pentane layer was then washed with 50 ml portions of water, 15% $NaHSO_3$ solution, and saturated $NaHCO_3$ solution, dried over anydrous $Na_2SO_4$, filtered, and heated on a rotating evaporator under reduced pressure at 0° C. to strip off the pentane. The residue was a yellow-green liquid which weighed 5.9 grams and assayed 97.1% by area % on the gas chromatograph. The crude % yield was 83.7%.

This reaction took a total of 29½ hours to go to completion. During the first two hours, the reaction mass did not have a phase transfer catalyst therein and only about 9 hours of the 29½ hours were at reflux. Nevertheless, the reaction ran quite slow even at 35°-40° C.

EXAMPLE X

This Example is a repeat of Example IX except that most of the hexane was distilled off during the course of the reaction.

N,N'-di-t-amylsulfamide (9.5 grams, 0.04 m) was weighed into a 3 neck 500 ml round bottom flask equipped with a magnetic stirrer, thermometer, and distilling head connected to a condenser and receiver. To the flask was added 40 ml of hexane, 0.5 grams of Adogen 464 phase transfer catalyst, and a solution of 10 grams of 50% NaOH in 150 grams of 13.9% NaClO. The flask was stoppered and lowered into a preheated oil bath (80° C.) and the reaction mass was stirred vigorously. The reaction was monitored at ½ hour intervals by gas chromatography. The gas chromatographic scans indicated that the reaction was completed in less than two hours. Little reaction occurred during the first ½ hour as the reaction mass warmed up to 65° C. and the hexane began to distill over. The conversion to di-t-amyldiazene was only about 15%. During the second half hour most of the hexane distilled over and the conversion increased to 52% as the reaction temperature increased to 75° C. The conversion increased to 95% over the third half hour and was completed by the time the two hour scan was run. The reaction was cooled back to room temperature and the hexane that was distilled off was added back to the reaction mixture. The bleach layer was separated from the hexane solution layer; then the hexane layer was washed with several 50 ml portions of water, 15% NaHSO$_3$ solution, saturated NaHCO$_3$ solution, and was dried over anhydrous Na$_2$SO$_4$. The solution was filtered and the hexane was stripped off on a rotating evaporator under reduced pressure at 10° C. The crude product weighed 5.4 grams and assayed 94.3% by area % on the gas chromatograph. The crude % yield was 74.5%.

What is claimed:

1. An improved process of preparing di-t-octyldiazene comprising oxidizing one equivalent of N,N'-di-t-octylsulfamide with at least two equivalents of sodium hypochlorite and 1.0 equivalent of sodium or potassium hydroxide at a temperature of 65°–90° C. in the presence of less than 4 parts of hydrocarbon or chlorinated hydrocarbon solvent per part N,N'-di-t-octylsulfamide for about 2 to 5 hours until completion of the reaction recovering the product in high purity and high yield.

2. The process of claim 1 where a phase transfer catalyst is added to reduce foaming.

3. The process of claim 2 where the crude product is washed with a freshly prepared aqueous sodium bisulfite solution to remove chloramine impurities.

4. The process of claim 1 where the solvent is removed during the oxidation step.

5. The process of claim 1 where the solvent is selected from the group consisting of hexane, pentane, heptane, cyclohexane, and methylene chloride.

* * * * *